(12) United States Patent
Katou

(10) Patent No.: US 9,492,142 B2
(45) Date of Patent: Nov. 15, 2016

(54) ULTRASONIC DIAGNOSTIC DEVICE

(75) Inventor: Yoshiki Katou, Tokyo (JP)

(73) Assignee: KONICA MINOLTA MEDICAL & GRAPHIC, INC., Tokyo (JP)

( * ) Notice: Subject to any disclaimer, the term of this patent is extended or adjusted under 35 U.S.C. 154(b) by 374 days.

(21) Appl. No.: 13/257,262

(22) PCT Filed: Feb. 19, 2010

(86) PCT No.: PCT/JP2010/001087
§ 371 (c)(1),
(2), (4) Date: Sep. 16, 2011

(87) PCT Pub. No.: WO2010/106737
PCT Pub. Date: Sep. 23, 2010

(65) Prior Publication Data
US 2012/0016241 A1   Jan. 19, 2012

(30) Foreign Application Priority Data

Mar. 17, 2009   (JP) .................................. 2009-064145

(51) Int. Cl.
*A61B 8/00* (2006.01)
*G01S 15/89* (2006.01)
*G01S 7/52* (2006.01)

(52) U.S. Cl.
CPC ......... *A61B 8/4281* (2013.01); *G01S 15/8959* (2013.01); *A61B 8/4405* (2013.01); *G01S 7/52046* (2013.01); *G01S 15/8977* (2013.01)

(58) Field of Classification Search
CPC .............. G01S 15/8959; G01S 15/8977; G01S 7/52046; A61B 8/4281
See application file for complete search history.

(56) References Cited

U.S. PATENT DOCUMENTS

| 4,387,597 | A | * | 6/1983 | Brandestini ..................... 73/626 |
| 5,259,384 | A | * | 11/1993 | Kaufman et al. ............. 600/442 |
| 5,381,385 | A | * | 1/1995 | Greenstein ..................... 367/140 |
| 5,924,986 | A | * | 7/1999 | Chandler et al. ............. 600/407 |

(Continued)

FOREIGN PATENT DOCUMENTS

| JP | 2001-258879 A | 9/2001 |
| JP | 2005-221321 A | 8/2005 |

(Continued)

OTHER PUBLICATIONS

Goldberg et al, Multilayer Piezoelectric Ceramics for Two-Diomensional Array Transducers, IEEE Transactions on Ultrasonics, Ferroelectrics and Frequency Control, vol. 41, No. 5 Sep. 1994, pp. 761-771.*

(Continued)

*Primary Examiner* — Unsu Jung
*Assistant Examiner* — Saurel J Selkin
(74) *Attorney, Agent, or Firm* — Holtz, Holtz & Volek PC

(57) ABSTRACT

In an ultrasonic diagnostic device S according to the present invention, a reference signal generation unit 30 generates a reference signal to be used in correlation processing based on a direct reception signal obtained by receiving a first ultrasonic signal prior to being transmitted to a subject. Consequently, the ultrasonic diagnostic device S configured in this manner is able to generate a more suitable reference signal.

9 Claims, 7 Drawing Sheets

(56) References Cited

U.S. PATENT DOCUMENTS

2002/0002333 A1\* 1/2002 Angelsen et al. ............ 600/443
2002/0007118 A1   1/2002 Adachi et al.
2008/0021328 A1\* 1/2008 Habu et al. .................. 600/459

FOREIGN PATENT DOCUMENTS

JP       2006-217943 A    8/2006
JP       2008-220652 A    9/2008

OTHER PUBLICATIONS

International Search Report dated Apr. 6, 2010 (and English translation thereof) in International Application No. PCT/JP2010/001087.

\* cited by examiner

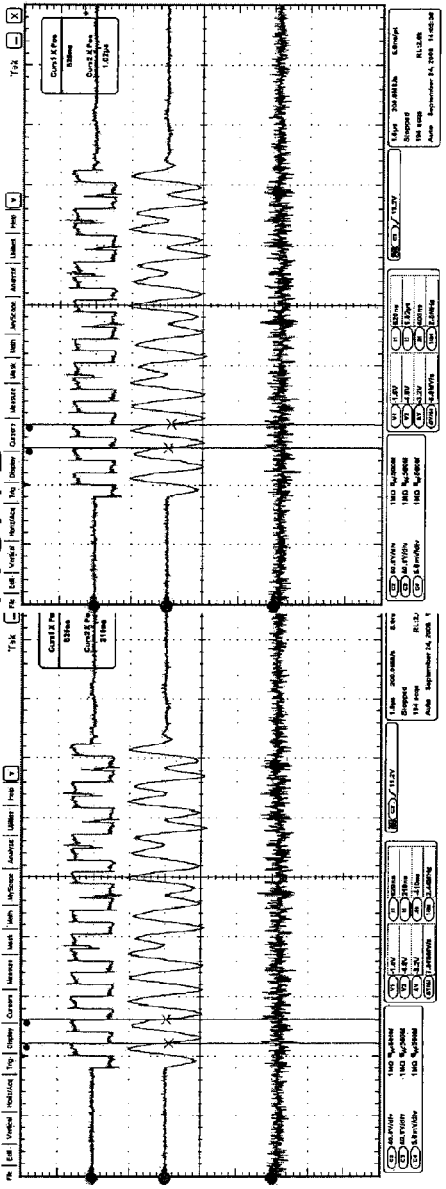
FIG. 7A SECOND WAVE  2.44MHz 410ns
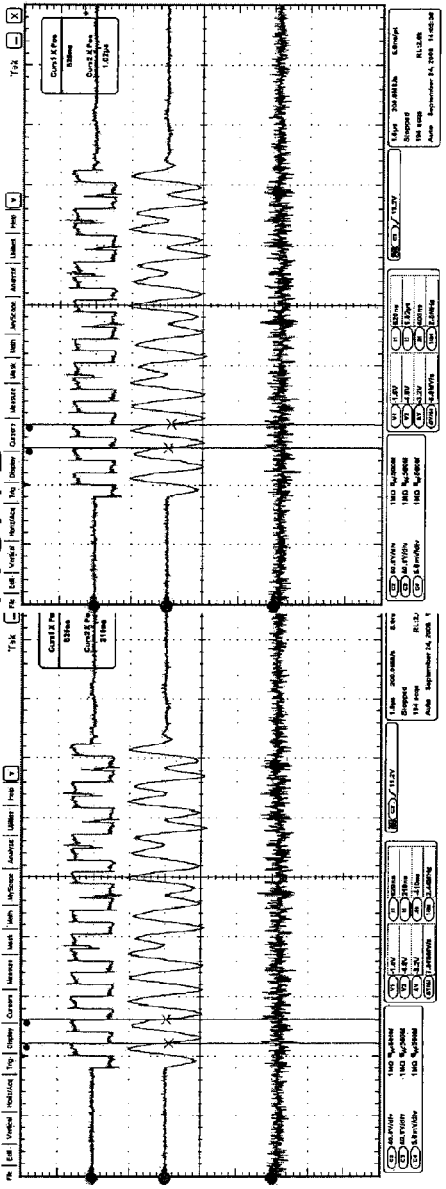
FIG. 7B THIRD WAVE  2.5MHz 400ns
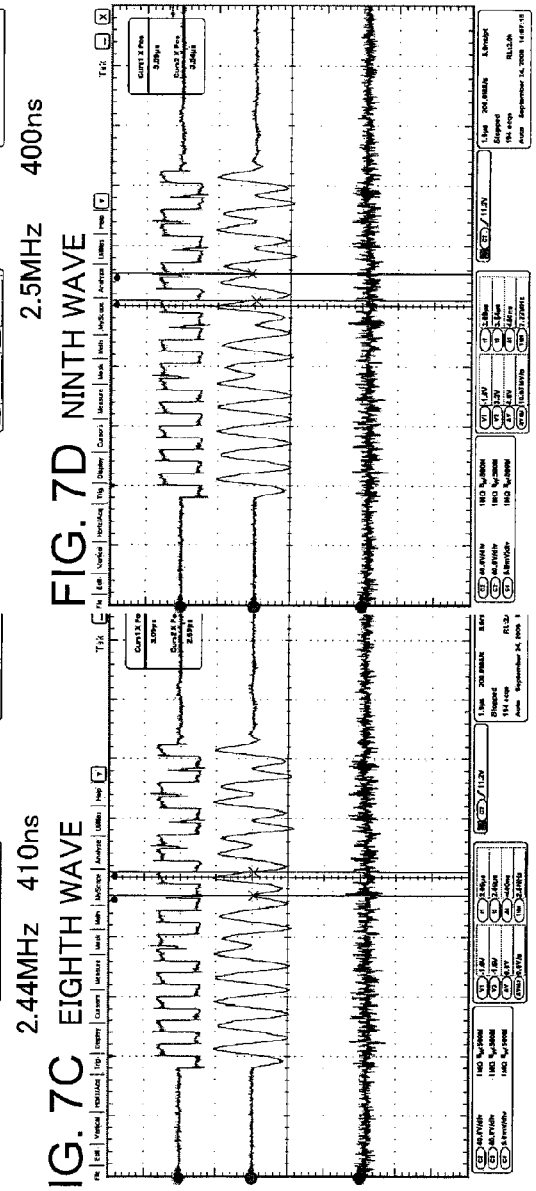
FIG. 7C EIGHTH WAVE  2.5MHz 400ns
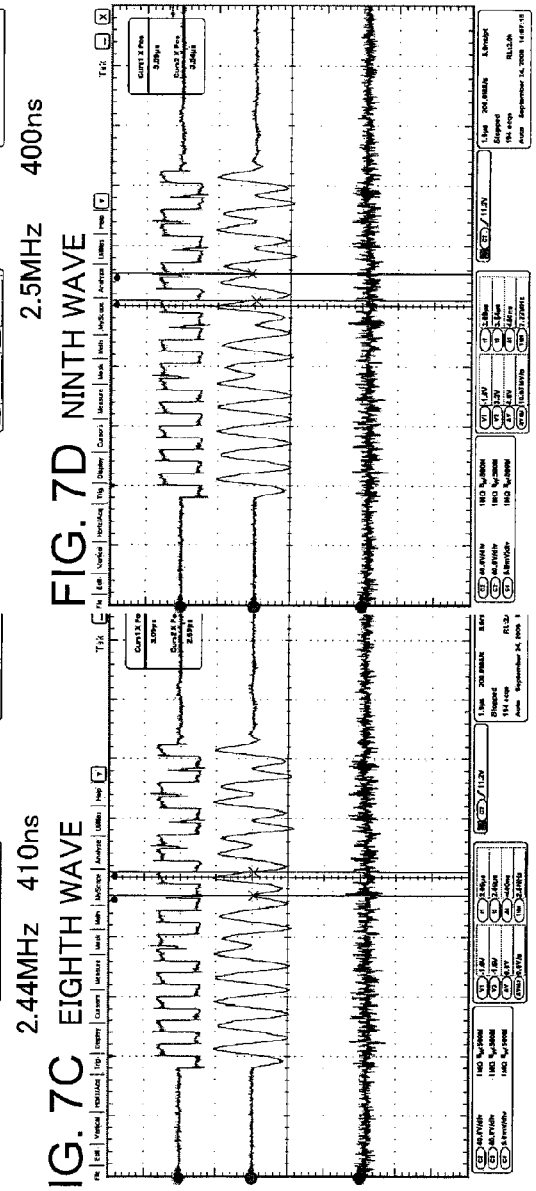
FIG. 7D NINTH WAVE  2.22MHz 450ns

ULTRASONIC DIAGNOSTIC DEVICE

This application is a U.S. National Phase Application under 35 USC 371 of International Application PCT/JP2010/001087 filed Feb. 19, 2010.

TECHNICAL FIELD

The present invention relates to an ultrasonic diagnostic device that transmits a first ultrasonic signal to a subject, receives a second ultrasonic signal from the subject based on the first ultrasonic signal, and forms an internal image of the subject based on the second ultrasonic signal, and more particularly, relates to an ultrasonic diagnostic device that detects the second ultrasonic signal from a reception signal obtained by receiving an ultrasonic signal from a subject by carrying out correlation processing on the reception signal and a prescribed reference signal.

BACKGROUND ART

Ultrasonic waves usually refer to waves of 16000 Hz or more, and since they enable non-destructive, harmless and essentially real-time examination of the inside of a body or material, they are applied in various fields such as detection of defects or diagnosis of disease. One of these applications is an ultrasonic diagnostic device used to generate images of the internal status within a subject by scanning the subject with ultrasonic waves and generating in image based on the reception signal generated from an ultrasonic wave (echo) reflected from the subject. This ultrasonic diagnostic device is compact and inexpensive in comparison with other medical imaging devices used in medical applications, is highly safe as a result of not causing radiation exposure associated with X-rays and the like, and offers various features such as display of blood flow using the Doppler effect. Consequently, ultrasonic diagnostic devices are widely used in fields such as circulatory organ (for example, diagnosis of the coronary artery of the heart), gastroenterology (for example, diagnosis of the stomach and intestines), internal medicine (for example, diagnosis of the liver, pancreas and spleen), urology (for example, diagnosis of the kidneys and urinary bladder) and obstetrics and gynecology. These ultrasonic diagnostic devices use an ultrasonic probe for transmitting and receiving ultrasonic waves (ultrasonic signals) to and from a subject. This ultrasonic probe is composed of one or more piezoelectric elements that generate ultrasonic waves (ultrasonic signals) by undergoing mechanical vibration based on a transmission electrical signal utilizing piezoelectric phenomena, and then generate a reception electrical signal by receiving a reflected ultrasonic wave (ultrasonic signal) generated due to mismatch of acoustic impedance within the subject.

As one aspect of this type of ultrasonic diagnostic device, research and development are being conducted on an ultrasonic diagnostic device that detects a second ultrasonic signal received from a subject based on a first ultrasonic signal transmitted to the subject by carrying out correlation processing on a reception signal obtained by receiving ultrasonic waves from the subject and a reference signal (template) for the purpose of receiving the second ultrasonic signal more accurately and/or observing deeper sites from the surface.

For example, in the ultrasonic diagnostic device disclosed in Patent Document 1, ultrasonic waves are diffused and transmitted to a prescribed three-dimensional region with an ultrasonic probe, a weighted matched filter, obtained by carrying out attenuation of ultrasonic waves corresponding to the distance from a reflection point to each ultrasonic transducer in a matched filter representing a correlation between a reflected wave from a prescribed reflection point contained in the prescribed three-dimensional region, is convoluted with a reception signal received by the ultrasonic probe to determine an image value at the prescribed reflection point, followed by determining volume data in the prescribed three-dimensional region by determining the image value of each reflection point. It is explained in paragraph [0020] of Patent Document 1 with respect to this matched filter that, "This matched filter is determined by the distance from each ultrasonic transducer of the ultrasonic probe to a prescribed reflection point and the speed of the propagating ultrasonic waves, and represents the correlation with a reflected wave from a prescribed reflection point received by each ultrasonic transducer. This matched filter is provided for each reflection point contained in the three-dimensional region."

In addition, in the ultrasonic signal detection method using a matched filter disclosed in Patent Document 2, for example, a bottom echo signal waveform or flaw echo signal waveform is used a reference signal of a matched filter, a white noise waveform or grass echo signal waveform is used as a noise signal of the matched filter, and the coefficient signal of the matched filter is set based on the reference signal and noise signal. It is explained in paragraph [0048] of Patent Document 2 with respect to this matched filter that, "A bottom echo signal waveform or flaw echo signal waveform of an actual subject is used as a reference signal.", and it is explained in paragraph [0054] of this document that, "A prediction signal from a system response is used as a reference signal". Namely, a reference signal is obtained in Patent Document 2 by actually measuring an echo of a subject or by predicting from a system response.

However, in an ultrasonic diagnostic apparatus that detects a target signal, namely a second ultrasonic signal, by correlation processing in this manner, in the case the reference signal is not optimized, S/N ratio cannot be expected to be improved in comparison with the case of not carrying out correlation processing, and since there is also the occurrence of artifacts, optimization of the reference signal waveform is important.

Although the above-mentioned Patent Document 1 contains a description of a matched filter corresponding to a reference signal waveform, a specific method for forming a template of the matched filter is not disclosed, thereby making it difficult to obtain an optimum matched filter.

In addition, although a reference signal can be generated according to the description of the above-mentioned Patent Document 2, in the case of actual measurement, since the actual subject that generates the reference signal does not always coincide with a subject undergoing testing, it is difficult to obtain an optimum reference signal. In addition, in the case of predicting from a system response, since this is merely a prediction, the generated reference signal is not necessarily optimal.

Patent Document 1: Japanese Unexamined Patent Publication No. 2008-220652

Patent Document 2: Japanese Unexamined Patent Publication No. 2005-221321

SUMMARY OF THE INVENTION

With the foregoing in view, an object of the present invention is to provide an ultrasonic diagnostic device capable of generating a more suitable reference signal.

In the ultrasonic diagnostic device according to the present invention, a reference signal used in correlation processing is generated based on a reception signal obtained directly by receiving a first ultrasonic signal prior to transmitting to a subject. Consequently, an ultrasonic diagnostic device employing such a configuration is able to generate a more suitable reference signal.

The above and other objects, characteristics and advantages of the present invention will be made clear from the following detailed description and appended drawings.

BRIEF DESCRIPTION OF THE DRAWINGS

FIG. 7 is a drawing showing disturbances in one channel of a transmission signal waveform.

MODES FOR CARRYING OUT THE INVENTION

The following provides an explanation of an embodiment according to the present invention. Furthermore, constituents having the same reference symbols indicate the same constituents in each of the drawings, and explanations thereof are omitted. In addition, reference symbols without suffixes are used to indicate generic constituents in the present description, while reference symbols with suffixes are used to indicate individual constituents.

Figure 1:
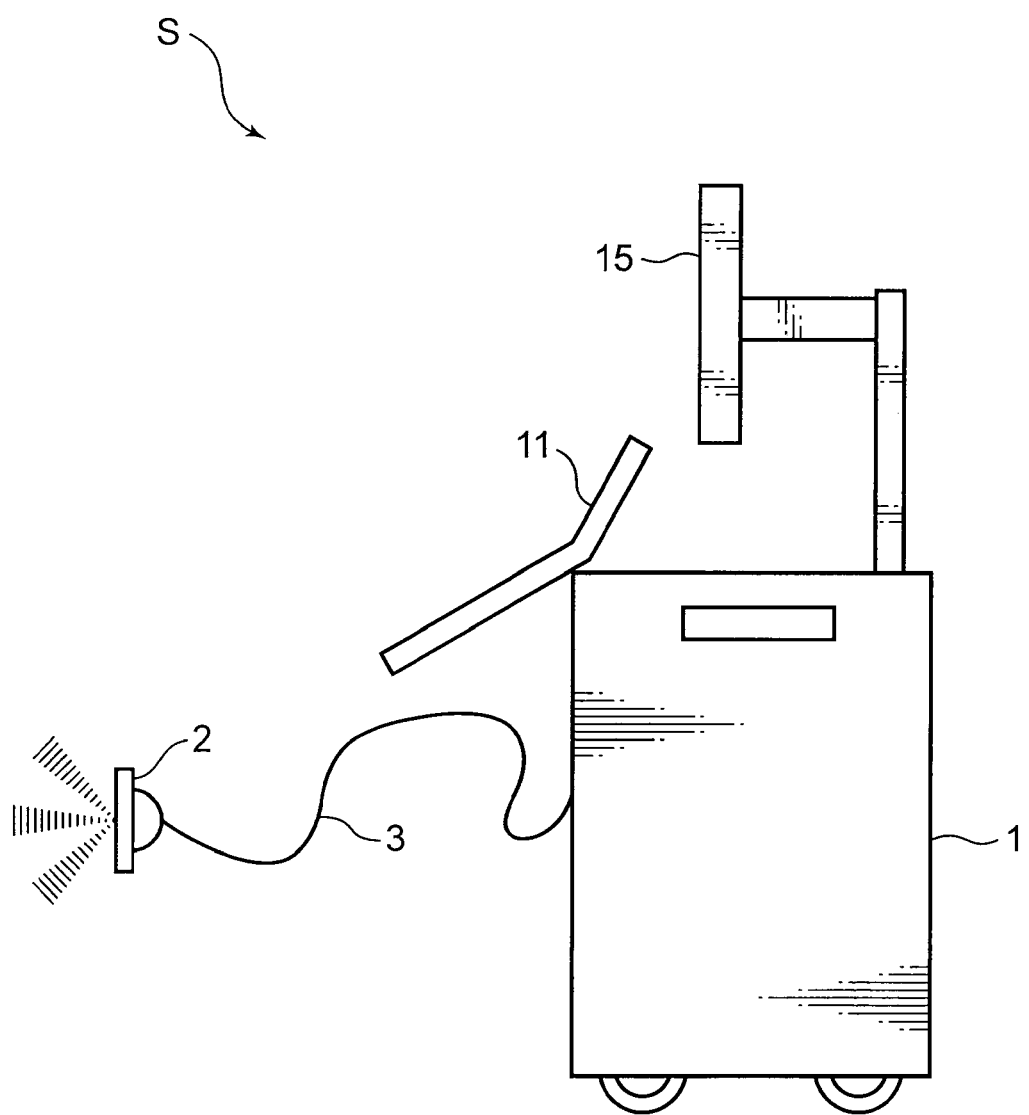
FIG. 1 is a drawing showing the external configuration of an ultrasonic diagnostic device in a first embodiment according to the present invention.
Figure 2:
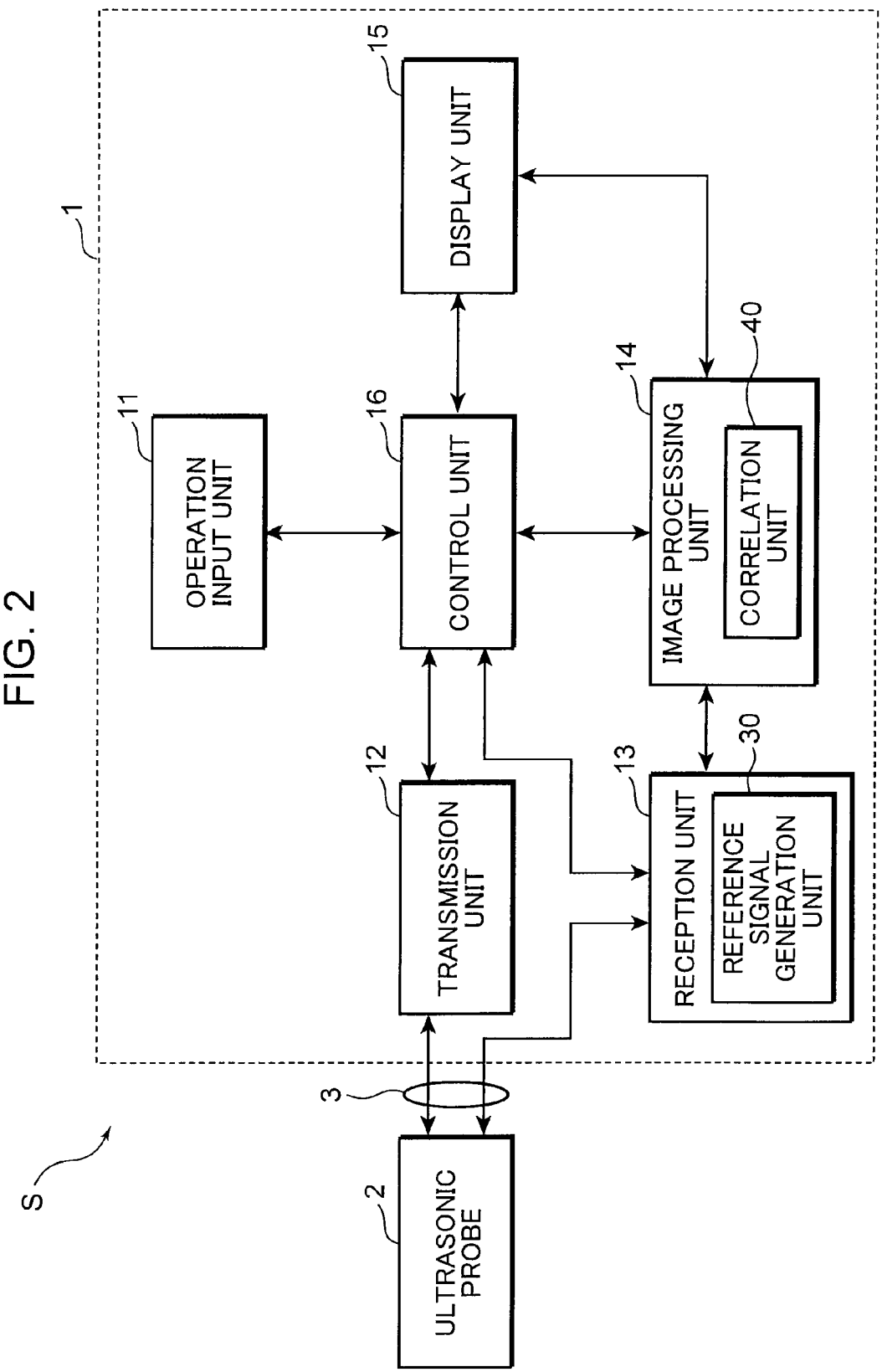
FIG. 2 is a block diagram showing the electrical configuration of the ultrasonic diagnostic device shown in FIG. 1.
Figure 3:
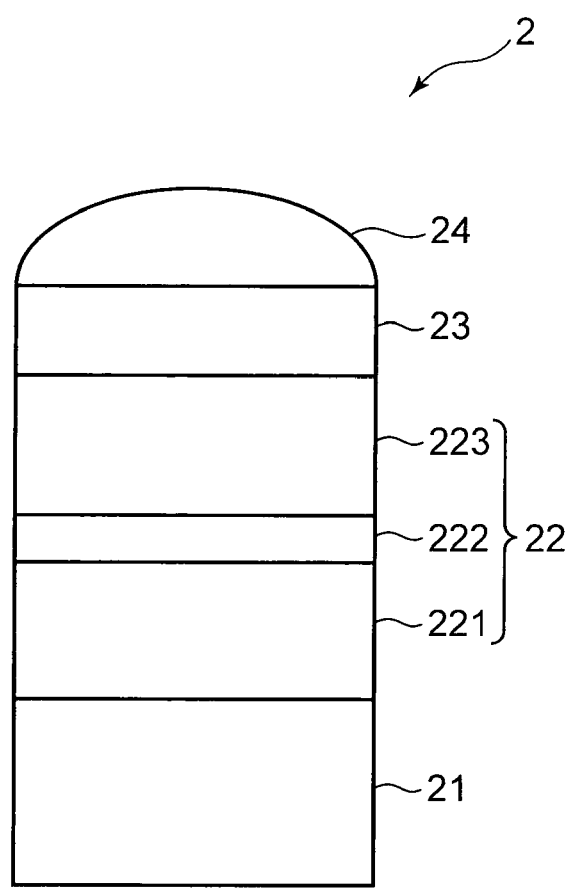
FIG. 3 is a cross-sectional view showing the configuration of an ultrasonic probe in the ultrasonic diagnostic device shown in FIG. 1.
Figure 4:
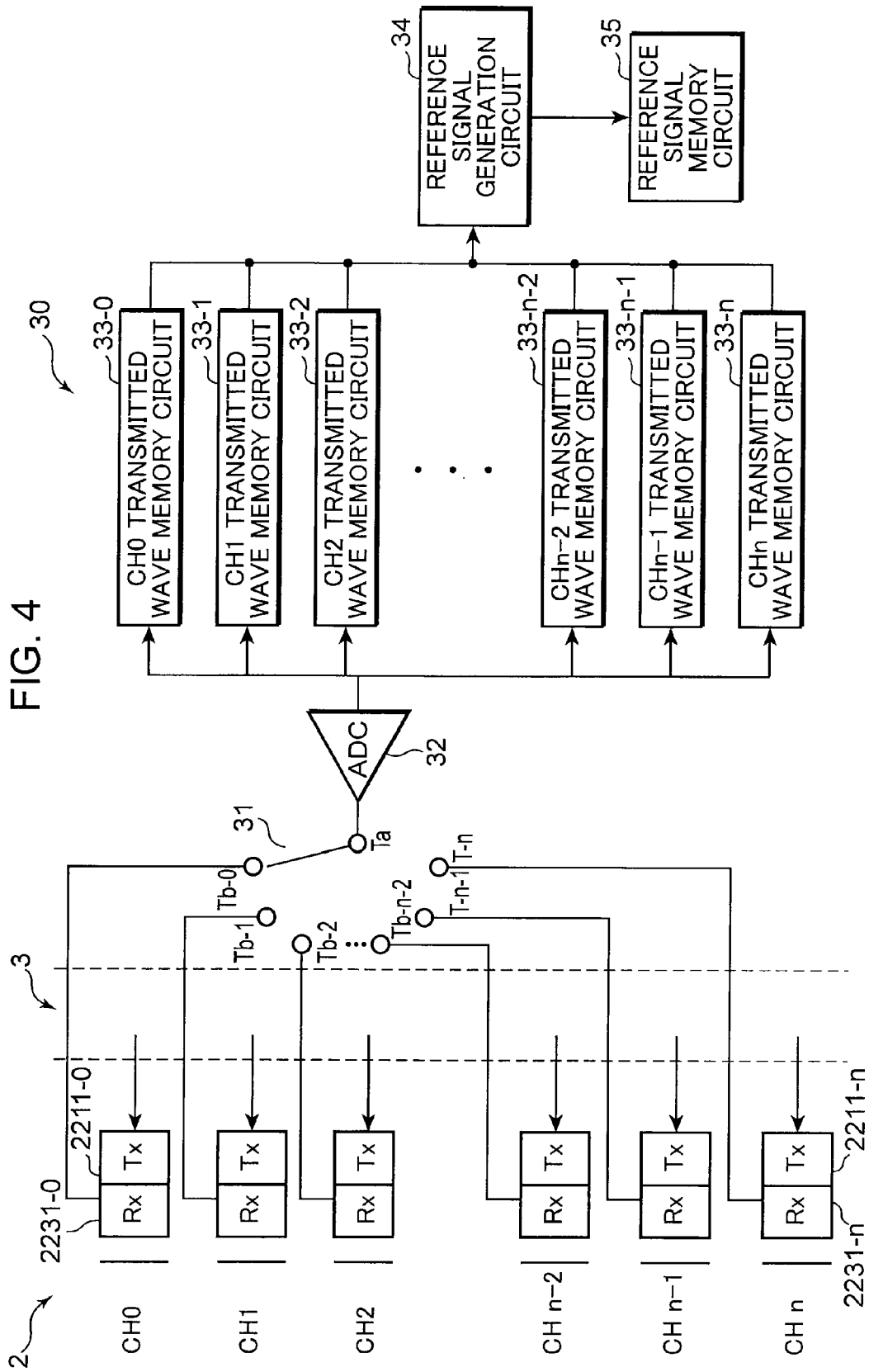
FIG. 4 is a block diagram showing the configuration of a reference signal generation unit in the ultrasonic diagnostic device shown in FIG. 1.

FIG. 1 is a drawing showing the external configuration of an ultrasonic diagnostic device in an embodiment. FIG. 2 is a block diagram indicating the electrical configuration of an ultrasonic diagnostic device in an embodiment. FIG. 3 is a drawing showing the configuration of an ultrasonic probe in an ultrasonic diagnostic device in an embodiment. FIG. 4 is a block diagram showing the configuration of a reference signal generation unit in an ultrasonic diagnostic device in an embodiment.

As shown in FIG. 1, an ultrasonic diagnostic device S is composed by being provided with an ultrasonic probe 2, which together with transmitting an ultrasonic wave (first ultrasonic signal) to a subject such as a body not shown, receives an ultrasonic wave (second ultrasonic signal) from the subject based on the first ultrasonic signal, and an ultrasonic diagnostic device body 1, which is connected to the ultrasonic probe 2 via a cable 3, transmits the first ultrasonic signal for the subject to the ultrasonic probe 2 by transmitting an electrical transmission signal to the ultrasonic probe 2 via the cable 3, and generates an image of the internal status of the subject in the form of an ultrasonic image based on an electrical reception signal generated with the ultrasonic probe 2 corresponding to the second ultrasonic signal from the subject received with the ultrasonic probe 2.

The ultrasonic wave from the subject based on the first ultrasonic signal is not only a reflected wave (echo) reflected by the first ultrasonic signal in the subject due to a mismatch of acoustic impedance within the subject, but is also an ultrasonic wave generated by microbubbles of an ultrasound contrast agent based on the first ultrasonic signal in the case of, for example, using an ultrasound contrast agent such as microbubbles. In the case of an ultrasound contrast agent, when the subject is irradiated with ultrasonic waves, the microbubbles of the ultrasound contrast agent vibrate sympathetically or resonate, and further disintegrate or disappear at a sound pressure equal to or greater than a fixed threshold value. In the case of an ultrasound contrast agent, ultrasonic waves occur due to the sympathetic vibration of microbubbles or the disintegration or disappearance of the microbubbles.

As shown in FIG. 2, for example, the ultrasonic diagnostic device body 1 is composed by being provided with an operation input unit 11, a transmission unit 12, a reception unit 13, an image processing unit 14, a display unit 15 and a control unit 16.

The operation input unit 11 is a device for inputting data such as a command for instructing start of diagnosis or personal information of a subject, and includes, for example, an operating panel provided with a plurality of input switches or keyboard.

The transmission unit 12 includes a circuit for generating the first ultrasonic signal in the ultrasonic probe 2 by supplying an electrical transmission signal to the ultrasonic probe 2 via the cable 3 under the control of the control unit 16. The transmission unit 12 is composed by being provided with a high-voltage pulse generator and the like that generates high-voltage pulses. In the case the ultrasonic probe 2 is composed by being provided with a plurality of piezoelectric elements, the transmission unit 12 is also provided with a transmission beam former and the like that generates drive signals by imparting a delay time with a delay circuit to pulses generated by the high-voltage pulse generator, for example, in order to transmit to a subject the first ultrasonic signal of a transmission beam obtained by the plurality of piezoelectric elements forming a main beam in a prescribed direction (prescribed bearing). The drive signals generated by the transmission unit 12 consist of a plurality of pulse signals for which a delay time has been individually and suitably set for each of the plurality of piezoelectric elements, and are respectively supplied to the plurality of piezoelectric elements in the ultrasonic probe 2 via the cable 3. As a result of the plurality of drive signals, the phase of the ultrasonic waves radiated from each piezoelectric element aligns in a specific direction (specific bearing) (or a specific transmission focus point), and the ultrasonic probe 2 generates the first ultrasonic signal of the transmission beam obtained by forming the main beam in that specific direction. The specific direction is represented by an angle that uses the direction normal to the transmission/reception plane of the ultrasonic signals formed by the plurality of piezoelectric elements as a reference angle (0 degrees). Examples of this type of electronic scanning system include linear scanning, sector scanning and convex scanning.

The first ultrasonic signal preferably has a unique waveform that is as redundant as possible and not found in the natural world in order to enhance noise resistance and easily distinguish the second ultrasonic signal based on the first ultrasonic signal from noise, for example. This type of first ultrasonic signal is, for example, a pulse obtained by using a spectral spread method. Examples of spectral spread methods include a frequency chirp method that changes frequency, a phase modulation method that modulates phase, or a hybrid method that combines a frequency chirp method and a phase modulation method. Examples of a frequency chirp method include a method in which a frequency is changed monotonously, such as linearly, at a prescribed ratio preset accompanying an elapsed time. An example of a phase modulation method is a method in which phase is modulated using a PN sequence. A PN sequence refers to a pseudo-random number sequence, and examples of PN sequences include Barker sequences, M sequences (maximal length sequences) and Gold sequences. Barker sequences in particular have the characteristic of demonstrating a peak in the case of a time delay of zero with an auto-correlation function while demonstrating a value of 0 or ±1 in the case of other time delays.

The reception unit 13 includes a circuit that receives an electrical reception signal from the ultrasonic probe 2 via the cable 3 under the control of the control unit 16, and outputs the reception signal to the image processing unit 14. The reception unit 13 is composed by being provided with an amplifier and the like for amplifying the reception signal at a preset and predetermined amplification rate in order to compensate for transmission loss (transfer loss) of the cable 3, for example. In the case the ultrasonic probe 2 is composed by being provided with a plurality of piezoelectric elements, a reception beam is formed by so-called rectifying addition during reception as well in the same manner as formation of the transmission beam during transmission. Namely, a delay time is suitably and individually set for a plurality of output signals respectively output from the plurality of piezoelectric elements in the ultrasonic probe 2, and the phase of each output signal is aligned in a specific direction (specific bearing) (or a specific reception focus point) by adding the plurality of delayed output signals, resulting in the formation of a main beam in that specific direction. In such a case, the reception unit 13 is also provided with a reception beam former and the like into which is input each of the output signals amplified by the amplifier.

The image processing unit 14 includes a circuit for forming an image representing an internal status of a subject based on the second ultrasonic signal from the subject based on the first ultrasonic signal received with the reception unit 13 under the control of the control unit 16. The image processing unit 14 is composed by being provided with, for example, a digital signal processor (DSP) that generates an ultrasonic image of a subject based on the output of the reception unit 13, and a digital-analog conversion circuit (DAC circuit) that converts a signal processed with the DSP from a digital signal to an analog signal in order to display the ultrasonic image on the display unit 15. The DSP is provided with, for example, a B mode processing circuit, a Doppler processing circuit and a color mode processing circuit, enabling the generation of so-called B mode images, Doppler images and color mode images.

The display unit 15 is a device for displaying an ultrasonic image of a subject generated with the image processing unit 14 under the control of the control unit 16. The display unit 15 is, for example, a display device such as a CRT display, liquid crystal display (LCD), organic EL display or plasma display, or a printing device such as a printer.

The control unit 16 is composed by being provided with, for example, a microprocessor, a storage device and peripheral circuits thereof, and includes a circuit for overall control of the ultrasonic diagnostic device S by respectively controlling the ultrasonic probe 2, the operation input unit 11, the transmission unit 12, the reception unit 13, the image processing unit 14 and the display unit 15 corresponding to their respective functions.

In addition, the ultrasonic probe 2 is a device for transmitting the first ultrasonic signal to a subject and receiving the second ultrasonic signal from the subject based on the transmitted first ultrasonic signal. As shown in FIG. 3, for example, the ultrasonic probe 2 is composed by being provided with a flat acoustic damping member (acoustic damping member, packing layer, damper layer) 21, a piezoelectric portion 22 laminated on one of the main surfaces of the acoustic damping member 21, an acoustic matching layer 23 laminated on the piezoelectric portion 22, and an acoustic lens 24 laminated on the acoustic matching layer 23.

The acoustic damping member 21 mechanically supports the piezoelectric portion 22 and applies acoustic damping to favorably maintain the acoustic properties of the piezoelectric portion 22, is composed of a material that absorbs ultrasonic waves (ultrasonic wave absorbing material), and mainly absorbs ultrasonic waves radiated from the piezoelectric portion 22 in the direction of the acoustic damping member 21.

The piezoelectric portion 22 includes a piezoelectric material, and is composed by being provided with one or a plurality of piezoelectric elements capable of mutually converting signals between electrical signals and ultrasonic signals by utilizing piezoelectric phenomena. In the present embodiment, the piezoelectric portion 22 includes a piezoelectric material and is composed by being provided with a plurality of piezoelectric elements capable of mutually converting signals between electrical signals and ultrasonic signals by utilizing piezoelectric phenomena, and the plurality of piezoelectric elements are, for example, arranged linearly and compose a one-dimensional linear array type ultrasonic transducer. Furthermore, the plurality of piezoelectric elements may also compose a two-dimensional array type ultrasonic transducer composed in the form of a two-dimensional array in which the piezoelectric elements are arranged in p rows×q columns in two mutually linear independent directions when viewed from overhead, such as in two mutually intersecting directions (wherein, p and q are integers). The piezoelectric elements are provided with a pair of mutually opposing electrodes consisting of a first electrode and a second electrode, and are composed by providing a piezoelectric material between the first electrode and the second electrode. The piezoelectric portion 22 converts a transmission signal input from the transmission unit 12 of the ultrasonic diagnostic device body 1 via the cable 3 to an ultrasonic signal, and together with transmitting the ultrasonic signal to a subject in the form of the first ultrasonic signal, converts the received second ultrasonic signal to an electrical signal and outputs this electrical signal (reception signal) to the reception unit 13 of the ultrasonic diagnostic device body 1 via the cable 3. As a result of placing the ultrasonic probe 2 in contact with a subject, the ultrasonic signal generated in the piezoelectric portion 22 is transmitted to the subject in the form of the first ultrasonic signal, and the second ultrasonic signal from the subject is received in the piezoelectric portion 22.

The ultrasonic probe 2 receives the first ultrasonic signal prior to being transmitted to the subject from the piezoelectric portion 22, and although a direct reception piezoelectric portion, which outputs a direct reception signal, obtained by directly receiving the first ultrasonic signal, to the reception unit 13 via the cable 3, may be provided separately from the piezoelectric portion 22, in the present embodiment, the piezoelectric portion 22 includes a piezoelectric material and is composed by being provided with first and second piezoelectric portions 221 and 223 capable of mutually converting signals between electrical signals and ultrasonic signals by utilizing piezoelectric phenomena, the first ultrasonic signal is transmitted by the first piezoelectric unit 221, the second ultrasonic signal is received by the second piezoelectric portion 223, and a direct reception signal is obtained by receiving the first ultrasonic signal transmitted by the piezoelectric portion 221 with the second piezoelectric portion 223 before being transmitted to the subject. The first piezoelectric portion 221 is composed by being provided with a plurality of first piezoelectric elements, while the second piezoelectric portion 223 is composed by being provided with a plurality of second piezoelectric elements. As a result of configuring in this manner, the first ultrasonic signal transmitted by the first piezoelectric portion 221 is received directly with the second piezoelectric portion 223 prior to being transmitted to the subject, thereby enabling the obtaining of a direct reception signal for generating a reference signal. In addition, since the second piezoelectric portion 223 serves to both receive the second ultrasonic signal and receive the first ultrasonic signal prior to being transmitted to the subject, the number of components can be reduced, thereby making it possible to reduce costs.

In addition, the second piezoelectric portion 223 is arranged in proximity to the first piezoelectric portion 221. By arranging the first and second piezoelectric portions 221 and 223 in mutual proximity in this manner, the first ultrasonic signal can be received more directly prior to being transmitted to the subject, and for example, a direct reception signal can be obtained in which external disturbances and noise are reduced.

Although a configuration may be employed in which the second piezoelectric portion 223 is arranged in a row adjacent to the first piezoelectric portion 221 in roughly the same plane by dividing a plurality of piezoelectric elements arranged in the form of a two-dimensional matrix, for example, into each region and using one of the regions for the second piezoelectric portion 223 and using the other region for the first piezoelectric portion 221 in order to arrange the first and second piezoelectric portions 221 and 223 in mutual proximity, in the present embodiment, the second piezoelectric portion 223 is arranged between the transmission-reception plane of the first and second ultrasonic signals (externally exposed surface of the acoustic lens 24) and the first piezoelectric portion 221. As a result of employing this configuration, the second piezoelectric portion 223 can be laminated directly or indirectly in the direction of the sound axis on the first piezoelectric portion 221, and the first ultrasonic signal can be received more directly prior to being transmitted to the subject, thereby allowing the obtaining of a direct reception signal in which external disturbances, noise and the like are further reduced. In addition, size can be reduced since the first and second piezoelectric portions 221 and 223 are laminated. In the present embodiment, the second piezoelectric portion 223 is laminated directly over the first piezoelectric portion 221 via an intermediate layer 222. The intermediate layer 222 is a member for laminating the first piezoelectric portion 221 and the second piezoelectric portion 223, and matches the acoustic impedance of the first piezoelectric portion 221 and the second piezoelectric portion 223.

The piezoelectric materials used to form the first and second piezoelectric portions 221 and 223 may both be inorganic piezoelectric materials, both organic piezoelectric materials, or one may be an inorganic piezoelectric material and the other an organic piezoelectric material. Examples of inorganic piezoelectric materials include so-called PZT, crystal quartz, lithium niobate ($LiNbO_3$), potassium tantalum niobate ($K(Ta,Nb)O_3$), barium titanate ($BaTiO_3$), lithium tantalate ($LiTaO_3$) and strontium titanate ($SrTiO_3$). A polymer of vinylidene fluoride, for example, can be used as an organic piezoelectric material. In addition, a vinylidene fluoride (VDF)-based copolymer can be used as an organic piezoelectric material. This vinylidene fluoride-based copolymer is a copolymer of vinylidene fluoride and another monomer, and examples of other monomers that can be used include ethylene trifluoride, tetrafluoroethylene, perfluoroalkyl vinyl ether (PFA) perfluoroalkoxyethylene (PAE) and perfluorohexaethylene. Since the electromechanical coupling constant (piezoelectric effect) in the direction of thickness changes according to the copolymerization ratio thereof, vinylidene fluoride-based copolymers are used at a suitable copolymerization ratio corresponding to the specifications and the like of the ultrasonic transducer. For example, in the case of a copolymer of vinylene fluoride and ethylene trifluoride, the copolymerization ratio of the vinylidene fluoride is preferably 60 mol % to 99 mol %, while in the case of a composite element in which an organic piezoelectric element is laminated on an inorganic piezoelectric element, the copolymerization ratio of vinylidene fluoride is more preferably 85 mol % to 99 mol %. In addition, in the case of such composite elements, the other monomer is preferably perfluoroalkyl vinyl ether (PFA), the other monomer is preferably perfluoroalkoxyethylene (PAE) or perfluorohexaethylene. In addition, polyurea can also be used as an organic piezoelectric material. In the case of this polyurea, the piezoelectric body is preferably produced by vapor deposition polymerization. Examples of monomers for use with polyurea include those having a structure represented with the general formula $H_2N-R-NH_2$. Here, R may include an alkylene group, phenylene group, divalent heterocyclic group or heterocyclic group optionally substituted with an arbitrary substituent. Polyurea may also be a copolymer of a urea derivative and another monomer. Preferable examples of polyurea include aromatic polyurea using 4,4'-diaminodiphenylmethane (MDA) and 4,4'-diphenylmethane diisocyanate (MDI). In the present embodiment, the second piezoelectric portion 223 is composed by being provided with an organic piezoelectric material. Consequently, it is able to receive ultrasonic signals over a comparatively wide band. Thus, the second ultrasonic signal of a higher harmonic wave can be received in response to a prescribed fundamental wave of the first ultrasonic signal, for example, and an ultrasonic image can be formed by, for example, so-called harmonic imaging technology.

The acoustic matching layer 23 is a member that matches the acoustic impedance of the piezoelectric portion 22 with the acoustic impedance of a subject. The acoustic lens 24 is a member that converges the first ultrasonic signal transmitted from the piezoelectric portion 22 towards the subject, and as shown in FIG. 3, for example, has the shape of a protruding arc. Furthermore, the acoustic matching layer 23 and the acoustic lens 24 may also be integrally composed.

What should be noted is that in the present embodiment, as shown in FIG. 2, the reception unit 13 is provided with a reference signal generation unit 30 that generates a reference signal (template) used in correlation processing for detecting the second ultrasonic signal based on a direct reception signal obtained by receiving the first ultrasonic signal prior to being transmitted to a subject, the image processing unit 14 is provided with a correlation unit 40 that detects the second ultrasonic signal from the output of the reception unit 13 by carrying out correlation processing between the output of the reception unit 13 and the reference signal preliminarily generated with the reference signal generation unit 30, and the image processing unit 14 forms an ultrasonic image of the subject based on the second ultrasonic signal detected as a result of correlation processing with the correlation unit 40.

In general, correlation processing is processing for determining the degree to which two waveforms are similar (degree of similarity, resemblance degree), and in the case of two series $x_n$ and $y_n$, for example, a value z indicated with the following formula 1 serves as an evaluation criterion, and the larger the value of z, the higher the degree of similarity between the two series:

$$z = \Sigma x_k y_k \quad (1)$$

wherein, $\Sigma$ determines the sum from k=1 to k=n.

In the correlation processing carried out in the ultrasonic diagnostic device S, a waveform assumed (presumed) to be the waveform of the second ultrasonic signal is taken to be the reference signal, and when correlation processing is carried out between the output of the reception unit 13 and the reference signal, a sharp peak is detected at the moment the reference signal and the second ultrasonic signal as the reception signal overlap. The larger the size of this peak, the greater the similarity between the reception signal and the reference signal. In the present embodiment, this reference signal is taken to be the first ultrasonic signal prior to being transmitted to the subject. For example, in the case this value of z is larger than a certain threshold value in order to remove noise, the second ultrasonic signal is made to be received at an intensity proportional to z, and the image processing unit 14 generates an ultrasonic image by determining delay time and signal intensity from this value of z.

The following provides a more detailed explanation of the reference signal generation unit 30. As shown in FIG. 4, for example, the reference signal generation unit 30 is composed by being provided with a switching circuit 31, an analog-digital conversion circuit (ADC) 32, a channel n transmitted wave memory circuit 33, a reference signal generation circuit 34 and a reference signal memory circuit 35.

The switching circuit 31 is a multiple-input, single-output switch that is used to switch channels. The switching circuit 31 is a circuit that selectively outputs from an output terminal Ta a single input signal among a plurality of n input signals respectively input to a plurality of n (where, n is an integer of 2 or more) input terminals Tb (Tb-0 to Tb-n) by connecting any one of the plurality of n input terminals Tb-0 to Tb-n to the output terminal Ta. The switching circuit 31 is at least provided with a plurality of n input terminals Tb-0 to Tb-n corresponding to a plurality of second piezoelectric elements 2231 in the second piezoelectric portion 223. This plurality of n input terminals Tb-0 to Tb-n is respectively connected to the plurality of second piezoelectric elements 2231 (2231-0 to 2231-n) in the second piezoelectric portion 223 of the ultrasonic probe 2 via the cable 3, and each reception signal respectively output from the plurality of second piezoelectric elements 2231-0 to 2231-n in the second piezoelectric portion 223 is input thereto.

The analog-digital conversion circuit 32 is a circuit that is connected to the output terminal Ta of the switching circuit 31, and converts analog reception signals output from the output terminal Ta of the switching circuit 31 to digital reception signals.

The channel n transmitted wave memory circuit (CHn transmitted wave memory circuit) 33 is a circuit that is connected to the analog-digital conversion circuit 32 and stores digital reception signals output from the analog-digital conversion circuit 32. The channel n transmitted wave memory circuit 33 (33-0 to 33-n) is at least provided in a quantity corresponding to the plurality of second piezoelectric elements 2231 in the second piezoelectric portion 223. Each of the channel n transmitted wave memory circuits 33-0 to 33-n respectively stores a plurality of direct reception signals obtained by respectively receiving the plurality of first ultrasonic signals respectively transmitted from the plurality of first piezoelectric elements 2211 in the first piezoelectric portion 221 of the ultrasonic probe 2 with the plurality of second piezoelectric elements 2231 in the second piezoelectric portion 223 prior to being transmitted to a subject. Namely, each of the channel n transmitted wave memory circuits 33-0 to 33-n respectively corresponds to the plurality of second piezoelectric elements 2231 in the second piezoelectric portion 223, and stores a waveform of a direct reception signal received by the corresponding second piezoelectric element 2231. For example, the channel 0 transmitted wave memory circuit 33-0 stores the waveform of a direct reception signal of channel 0 obtained by receiving the first ultrasonic signal of channel 0 transmitted from the first piezoelectric element 2211-0 of channel 0 (CH 0) with the second piezoelectric element 2231-0 of channel 0 prior to being transmitted to the subject, and for example, the channel 1 transmitted wave memory circuit 33-1 stores the waveform of a direct reception signal of channel 1 obtained by receiving the first ultrasonic signal of channel 1 transmitted from the first piezoelectric element 2211-1 of channel 1 (CH1) with the second piezoelectric element 2231-1 of channel 1 prior to being transmitted to the subject.

The reference signal generation circuit 34 is a circuit that is connected to the plurality of channel n transmitted wave memory circuits 33-0 to 33-n, and generates a reference signal used in correlation processing based on a plurality of direct reception signals respectively stored in the plurality of channel n transmitted wave memory circuits 33-0 to 33-n.

More specifically, the reference signal generation circuit 34 generates a reference signal by, for example, averaging a plurality of n direct reception signals obtained by respectively receiving a plurality of n first ultrasonic signals respectively transmitted by the plurality of n first piezoelectric elements 2211-0 to 2211-n prior to be transmitted to a subject, and using this average value as a reference signal. The average value is calculated by chronologically aligning, synchronizing and adding each of the direct reception signals and then dividing the sum by the number of direct reception signals. As a result of employing this configuration, even if there are variations in the properties of the plurality of first piezoelectric elements 2211 attributable to, for example, the production process or deterioration over time, these variations among elements are alleviated, allowing the obtaining of a more suitable reference signal. Furthermore, the average value may be a value obtained by determining the average for all of the plurality of n direct reception signals, or may be a value obtained by determining the average for only a portion of the direct reception signals among the plurality of direct reception signals. Alternatively, a deviation of each direct reception signal may be calculated after synchronizing the timing thereof, and the average value of the remaining direction reception signals may be calculated by excluding the direct reception signal having the largest deviation and the direct reception signal having the smallest deviation when calculating the average value in order to exclude abnormal values.

In addition, for example, the reference signal generation circuit 34 generates a reference signal by mutually comparing each waveform of a plurality of n direct reception signals obtained by respectively receiving a plurality of n first ultrasonic signals respectively transmitted by the plurality of n first piezoelectric elements 2211-0 to 2211-$n$ prior to being transmitted to a subject, and using as a reference signal the direct reception signal having the waveform for which there is the greatest frequency of roughly mutual agreement among the compared waveforms. This mutual comparison of each waveform can use a correlation operation that determines a correlation value for each pair of waveforms after synchronizing the timing thereof, and whether or not waveforms substantially coincide can be determined on the basis of the determined correlation value. As a result of configuring in this manner as well, even if there are variations in the properties of the plurality of first piezoelectric elements 2211 attributable to, for example, the production process or deterioration over time, these variations among elements are alleviated, allowing the obtaining of a more suitable reference signal.

The reference signal memory circuit 35 is a circuit that is connected to the reference signal generation circuit 34, and stores reference signals generated by the reference signal generation circuit 34. Reference signals stored in the reference signal memory circuit 35 are read by the correlation unit 40 and used in correlation processing of the correlation unit 40.

In the ultrasonic diagnostic device S employing this configuration, at the time of diagnosis, for example, when an instruction to start diagnosis is input from the operation input unit 11, an electrical transmission signal is generated by the transmission unit 12 under the control of the control unit 16. This generated electrical transmission signal is supplied to the ultrasonic probe 2 via the cable 3. More specifically, this electrical transmission signal is supplied to the first piezoelectric portion 221 in the ultrasonic probe 2, and in the first piezoelectric portion 221, is respectively supplied at a prescribed delay time to the plurality of first piezoelectric elements 2211-0 to 2211-$n$ in the first piezoelectric portion 221. The first piezoelectric elements 2211 expand and contact in the direction of the thickness thereof as a result of being supplied with this electrical transmission signal, and undergo ultrasonic vibration corresponding to this electrical transmission signal. As a result of this ultrasonic vibration, the first piezoelectric elements 2211 radiate the first ultrasonic signal. After having been radiated from the first piezoelectric elements 2211 in the direction of the acoustic damping member 21, the first ultrasonic signal is absorbed by the acoustic damping member 21. In addition, after having been radiated from the first piezoelectric elements 2211 in the direction of the acoustic matching layer 23, the first ultrasonic signal is radiated through the acoustic matching layer 23 and the acoustic lens 24. When the ultrasonic probe 2 is placed in contact with a subject, for example, the first ultrasonic signal is transmitted to the subject from the ultrasonic probe 2 as a result thereof.

Furthermore, the ultrasonic probe 2 may be used by placing in contact with the surface of the subject, or may be used by inserting into a subject such as inserting into a body cavity.

Ultrasonic waves transmitted to the subject are reflected at one of a plurality of interfaces having different acoustic impedance in the subject and become reflected ultrasonic waves. Alternatively, in the case of injecting an ultrasound contrast agent into the subject, ultrasonic waves originating from the first ultrasonic signal are generated by the ultrasound contrast agent. These ultrasonic waves are received by the ultrasonic probe 2. More specifically, the ultrasonic waves are received by the second piezoelectric elements 2231 of the second piezoelectric portion 223 through the acoustic lens 24 and the acoustic matching layer 23. Namely, the ultrasonic waves are received by the second piezoelectric elements 2231, mechanical vibrations in the second piezoelectric elements 2231 are converted to an electrical signal, and that electrical signal is acquired in the form of a reception signal.

The electrical reception signal acquired from the second piezoelectric portion 223 is then received by the reception unit 13 via the cable 3 under the control of the control unit 16. The reception unit 13 carries out reception processing on the input reception signal, and more specifically, outputs to the correlation unit 40 of the image processing unit 14 after having been amplified, for example. The second ultrasonic signal is then detected by carrying out correlation processing between the output of the reception unit 13 in the correlation unit 40 and a reference signal (template) stored in the reference signal memory circuit 35.

Here, in the above description, the first ultrasonic signal is sequentially transmitted from the first piezoelectric portion 221 towards the subject and the second ultrasonic signal reflected in the subject is received by the second piezoelectric portion 223 in order to carry out electronic scanning while changing the bearing and focus depth (observation point).

The image processing unit 14 generates an ultrasonic image of the subject from the time from transmission to reception or signal intensity and the like based on the reception signal received by the reception unit 13 and subjected to correlation processing in the correlation unit 40 under the control of the control unit 16, and the display unit 15 displays the ultrasonic image of the subject generated by the image processing unit 14 under the control of the control unit 16.

A reference signal is generated according to the following operation prior to this diagnosis. Furthermore, generation of the reference signal is suitably executed for each diagnosis, for each prescribed time period or prescribed number of diagnoses, or in the case of generating a plurality of ultrasonic images during diagnosis, during that generation.

First, a transmission signal sequentially generated by the transmission unit 12 is sequentially supplied to the plurality of n first piezoelectric elements 2211-0 to 2211-$n$ in the first piezoelectric portion 221 of the ultrasonic probe 2 via the cable 3, and the plurality of n first piezoelectric elements 2211-0 to 2211-$n$ sequentially radiate the first ultrasonic signal according to this transmission signal. This sequentially radiated first ultrasonic signal is sequentially received by the plurality of n second piezoelectric elements 2231-0 to 2231-$n$ respectively corresponding to the plurality of n first piezoelectric elements 2211-0 to 2211-$n$ prior to being transmitted into a subject, and is sequentially acquired as a direct reception signal. The plurality of n second piezoelectric elements 2231-0 to 2231-$n$ sequentially output this sequentially acquired direct reception signal to the reference signal generation unit 30 in the reception unit 13 of the ultrasonic diagnostic device body 1 via the cable 3. In the reference signal generation unit 30, the switching circuit 31 sequentially switches the connection between the output terminal Ta and each of the input terminals Tb-0 to Tb-$n$ in synchronization with the transmission signal sequentially generated by the transmission unit 12, and a plurality of n direct reception signals sequentially generated by the plurality of n second piezoelectric elements 2231-0 to 2231-$n$ are sequentially output from the output terminal Ta. The plurality of n direct reception signals sequentially output from the switching circuit 31 are sequentially stored in the plurality of n channel n transmitted wave memory circuits 33-0 to 33-$n$ via the analog-digital conversion circuit 32.

Namely, the transmission signal of channel 0 is first generated by the transmission unit 12, and the transmission signal of this channel 0 is supplied to the first piezoelectric element 2211-0 of channel 0 via the cable 3. The output terminal Ta is then connected to the input terminal Tb-0 of channel 0 in the switching unit 31 in synchronization therewith. The first ultrasonic signal of channel 0 is generated by the first piezoelectric element 2211-0 of channel 0 that has received supply of the transmission signal of channel 0, and this first ultrasonic signal is received by the second piezoelectric element 2231-0 of channel 0 prior to being transmitted to the subject to obtain a direct reception signal of channel 0. This direct reception signal of channel 0 is then output to the channel 0 transmitted wave memory circuit 33-0 via the cable 3, the switching circuit 31 and the analog-digital conversion circuit 32, where it is stored in the channel 0 transmitted wave memory circuit 33-0. When this processing of channel 0 is completed, a transmission signal of the next channel 1 is generated by the transmission unit 12 and this transmission signal of channel 1 is then supplied to the first piezoelectric element 2211-1 of channel 1 via the cable 3 in the same manner as channel 0 in order to carry out processing on channel 1. The output terminal Ta is then connected to the input terminal Tb-1 of channel 1 in the switching circuit 31 in synchronization therewith. The first ultrasonic signal of channel 1 is then generated by the first piezoelectric element 2211-1 of channel 1 that has received supply of the transmission signal of channel 1, and this first ultrasonic signal is received by the second piezoelectric element 2231-1 of channel 1 prior to being transmitted into the subject to obtain a direct reception signal of channel 1. This direct reception signal of channel 1 is then output to the channel 1 transmitted wave memory circuit 33-1 via the cable 3, the switching circuit 31 and the analog-digital conversion circuit 32 where it is stored in the channel 1 transmitted wave memory circuit 33-1. When this processing of channel 1 is completed, processing is similarly carried out on the next channel 2, and this processing is continued to be executed through channel n.

As a result of this operation, the plurality of n first ultrasonic signals sequentially generated by the plurality of n first piezoelectric elements 2211-0 to 2211-$n$ are sequentially received by the plurality of n second piezoelectric elements 2231-0 to 2231-$n$ prior to being transmitted to a subject, the plurality of n direct reception signals sequentially obtained as a result of reception thereof are sequentially output to the reference signal generation unit 30, and the connection between the output terminal Ta and each of the input terminals Tb-0 to Tb-n are sequentially switched in the switching circuit 31 in synchronization with generation of transmission signals for generating the first ultrasonic signals, thereby resulting in the plurality of n direct reception signals being sequentially stored in the plurality of n channel n transmitted wave memory circuits 33-0 to 33-$n$ corresponding to the channel number.

When a direct reception signal of each channel has been obtained, the reference signal generation circuit 34 generates a reference signal based on the plurality of n direct reception signals respectively stored in the plurality of n channel n transmitted wave memory circuits 30-0 to 33-$n$. The reference signal is generated by, for example, averaging the plurality of n direct reception signals as previously described. In addition, the reference signal is generated by, for example, mutually comparing each of the waveforms of the plurality of n direct reception signals and detecting the direct reception signal having a waveform that demonstrates the highest frequency. The generated reference signal is then output from the reference signal generation circuit 34 to the reference signal memory circuit 35 where it is stored in the reference signal memory circuit 35. Reference signals stored in the reference signal memory circuit 35 are read by the correlation unit 40 and used as a template for a matched filter that carries out correlation processing on the output of the reception unit 13.

As a result of operating in this manner, in the ultrasonic diagnostic device S of the present embodiment, a reference signal (template) is generated based on a direct reception signal obtained by receiving a first ultrasonic signal prior to being transmitted to a subject. Consequently, a more suitable reference signal is obtained. As a result, S/N ratio can be expected to be improved and the occurrence of artifacts is further reduced in comparison with the case of not carrying out correlation processing.

Figure 5A:
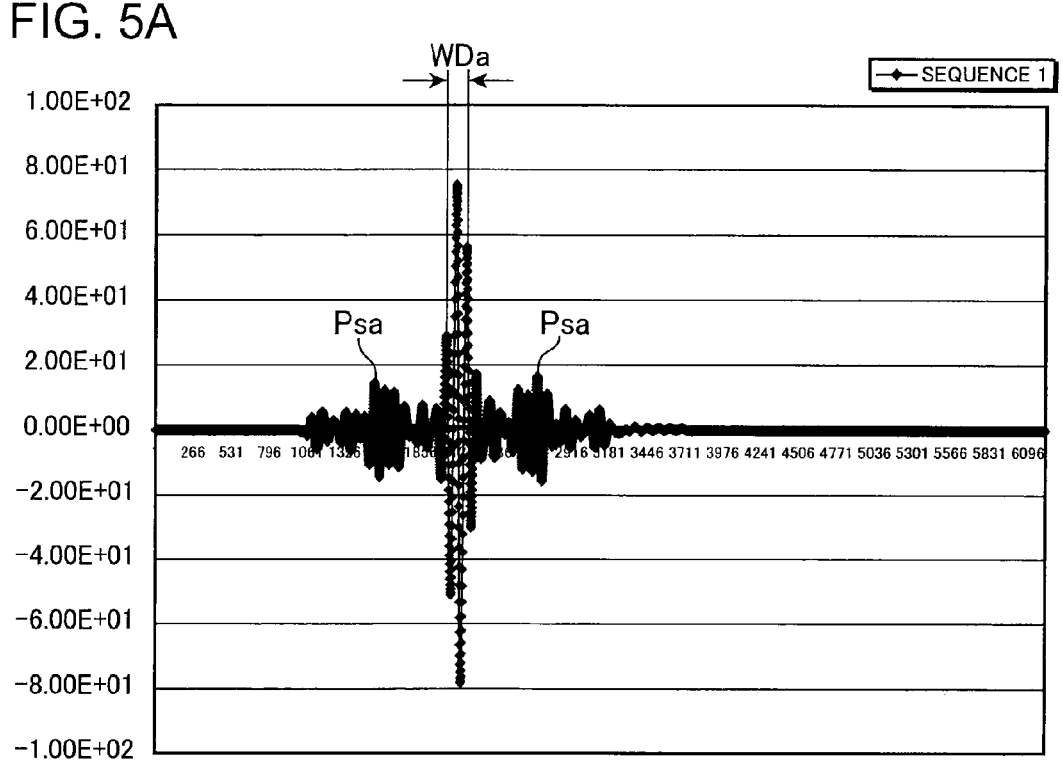
FIG. 5 is a drawing indicating experimental results in the case of using a Barker code 13_length PSK having a period of 2.5 MHz for a transmission signal.
Figure 5B:
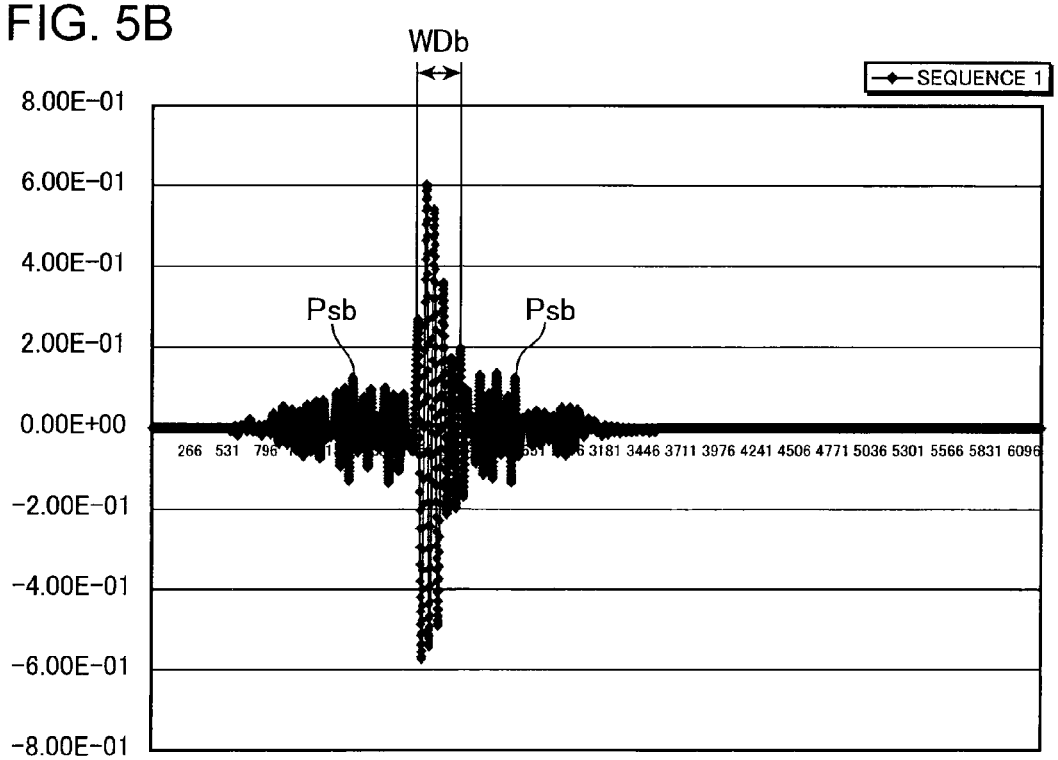
Figure 6A:
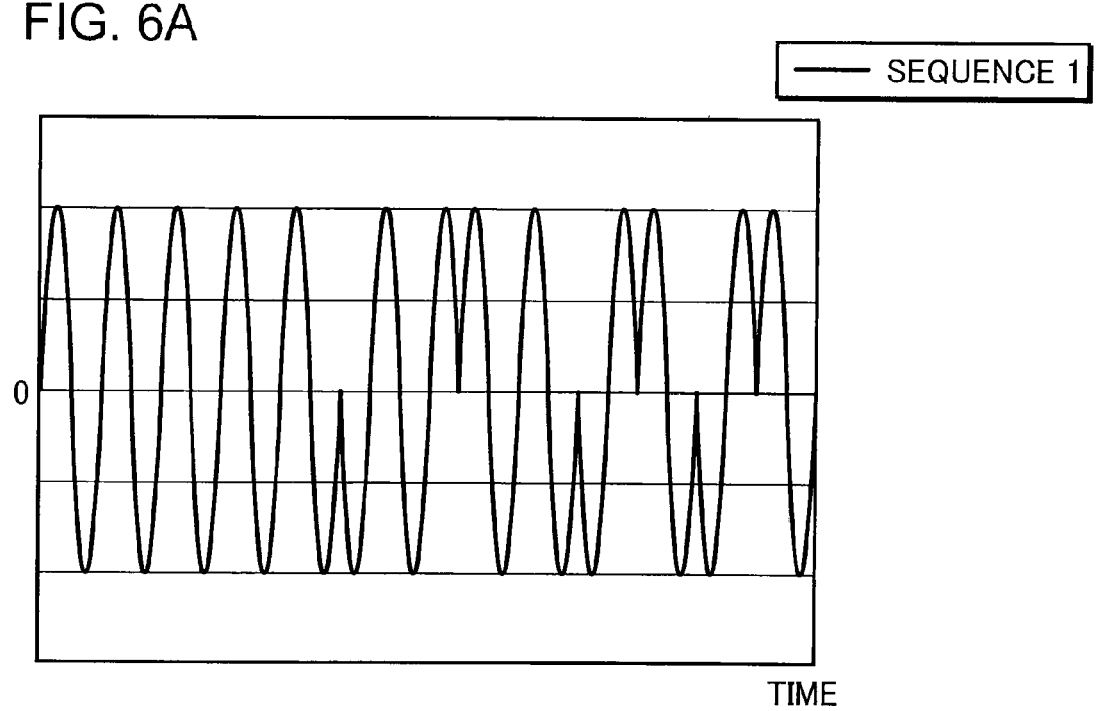
FIG. 6 is a drawing for explaining a Barker code 13_length PSK having a period of 2.5 MHz.
Figure 6B:
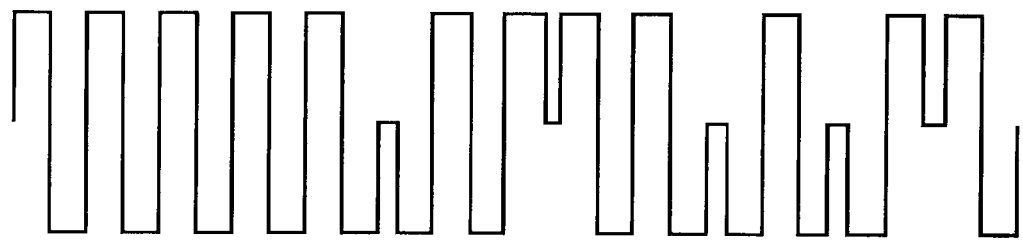

FIG. 5 is a drawing showing experimental results in the case of using a Barker code 13_length PSK having a period of 2.5 MHz for the transmission signal. FIG. 5A shows experimental results in the case of using a reference signal based on a direct reception signal in a matched filter, while FIG. 5B shows experimental results in the case of using a Barker code 13_length PSK having a period of 2.5 MHz in a matched filter. In FIG. 5, time is plotted on the horizontal axis while signal level is plotted on the vertical axis. FIG. 6 is a drawing for explaining a Barker code 13_length PSK having a period of 2.5 MHz. FIG. 6A shows the waveform of the Barker code 13_length PSK having a period of 2.5 MHz, while FIG. 6B shows the waveform of a square wave used to generation a transmission signal having the waveform shown in FIG. 6A. In FIG. 6, time is plotted on the horizontal axis while signal level is plotted on the vertical axis. FIG. 7 is a drawing showing disturbances in one channel of a transmission signal waveform. FIG. 7A indicates the case of a second wave, FIG. 7B the case of a third wave, FIG. 7C the case of an eighth wave, and FIG. 7D the case of a ninth wave. In FIG. 7, time is plotted on the horizontal axis while signal level is plotted on the vertical axis.

Although the transmission signal for generating the first ultrasonic signal may be arbitrary, the following explanation is provided for the case of, for example, using a Barker code 13_length PSK having a period of 2.5 MHz for the transmission signal.

A transmission waveform using a Barker code 13_length PSK having a period of 2.5 MHz has the waveform shown in FIG. 6A, and although this waveform may be generated with a circuit provided with a digital-analog conversion circuit and a linear amplification circuit, a circuit that converts a square wave having the waveform shown in FIG. 6B to a sine wave with a waveform shaping circuit is used for the purpose of reducing costs. This circuit is subjected to disturbances caused by circuit variations and the like even if the period of the waveform is one channel. For example, as shown in FIGS. 7A to 7D, although the period is 2.5 MHz in the third and eighth waves, the period of the second wave is shifted from 2.5 MHz to 2.44 MHz, while the period of the ninth wave is shifted from 2.5 MHz to 2.22 MHz.

Consequently, in the case of using a Barker code 13_length PKS having a period of 2.5 MHz used for a transmission signal in a matched filter for correlation processing, as shown in FIG. 5B, a plurality of peaks are comparatively frequently observed in the vicinity of peak Pb exhibiting the maximum signal level at a signal level roughly equal thereto. When considering lines that outline this peak, a width WDb of the peak Pb extends up spreading out. Moreover, a plurality of subpeaks Psb also having comparatively high signal levels are present on both sides of the peak Pb and slightly separated from the peak Pb.

On the other hand, in the case of using a reference signal based on a direct reception signal obtained by receiving the first ultrasonic signal prior to being transmitted to a subject in a matched filter, as shown in FIG. 5A, the number of peaks in the vicinity of a peak Pa exhibiting the maximum signal level having a signal level roughly equal thereto is fewer than in FIG. 5B. When considering lines that outline this peak, the peak Pa is comparatively sharp and a width WDa of the peak Pa is narrower than in FIG. 5B. The signal levels of a plurality of subpeaks Psa on both sides of the peak Pa and slightly separated from the peak Pa are also lower. Furthermore, the scales of the vertical axes in FIGS. 5A and 5B are different.

Thus, a reference signal (template) generated based on a direct reception signal results in a more suitable reference signal, and as a result, S/N ratio can be expected to be improved and occurrence of artifacts is further reduced.

Although the present description has disclosed various aspects of the technology as previously described, the main aspects of this technology are as summarized below.

The ultrasonic diagnostic device according to one aspect of the present invention is an ultrasonic diagnostic device provided with: a transmission unit for transmitting a first ultrasonic signal to a subject; a reception unit for receiving a reception signal by ultrasonic waves; and an image processing unit for forming an internal image of the subject based on a second ultrasonic signal from the subject based on the first ultrasonic signal received by the reception unit, and this device is further provided with: a reference signal generation unit for generating a reference signal to be used in correlation processing, based on a direct reception signal obtained by receiving the first ultrasonic signal prior to being transmitted to the subject; and a correlation unit for detecting the second ultrasonic signal from the output of the reception unit by carrying out correlation processing between the output of the reception unit and the reference signal preliminarily generated by the reference signal generation unit. The ultrasonic diagnostic device according to one aspect of the present invention is provided with: a transmission unit for transmitting a first ultrasonic signal to a subject; a reception unit for receiving a reception signal by ultrasonic waves; a reference signal generation unit for generating a reference signal used in correlation processing, based on a direct reception signal obtained by receiving the first ultrasonic signal prior to being transmitted to the subject; a correlation unit for detecting a second ultrasonic signal from the output of the reception unit by carrying out correlation processing between the output of the reception unit and the reference signal preliminarily generated by the reference signal generation unit; and an image processing unit for forming an internal image of the subject based on the second ultrasonic signal detected with the correlation unit.

In an ultrasonic diagnostic device configured in this manner, the reference signal used in correlation processing is generated based on a direct reception signal obtained by receiving the first ultrasonic signal prior to being transmitted to the subject. Consequently, an ultrasonic diagnostic device configured in this manner allows the obtaining of a more suitable reference wave, and as a result thereof, S/N ratio can be expected to be improved and the occurrence of artifacts is further reduced in comparison with the case of not carrying out correlation processing.

In addition, in another aspect, the above-mentioned ultrasonic diagnostic device is further provided with an ultrasonic probe provided with first and second piezoelectric portions that are formed of a piezoelectric material and that are capable of mutually converting signals between electrical signals and ultrasonic signals by utilizing piezoelectric phenomena, wherein the first ultrasonic signal is transmitted by the first piezoelectric portion, and the direct reception signal is a signal obtained by receiving the first ultrasonic signal transmitted by the first piezoelectric portion in use of the second piezoelectric portion prior to being transmitted to the subject.

An ultrasonic diagnostic device configured in this manner is able to directly receive the first ultrasonic signal transmitted by the first piezoelectric portion with the second piezoelectric portion prior to being transmitted to the subject, thereby allowing the obtaining of a direct reception signal for generating a reference signal.

In addition, in the above-mentioned ultrasonic diagnostic device of another aspect, the first piezoelectric portion is provided with a plurality of first piezoelectric elements, and the reference signal generation unit averages a plurality of direct reception signals obtained by respectively receiving a plurality of the first ultrasonic signals respectively transmitted by the plurality of first piezoelectric elements prior to being transmitted to the subject, and uses that average value as the reference signal.

In an ultrasonic diagnostic device configured in this manner, in the case the first piezoelectric portion is composed by being provided with a plurality of first piezoelectric elements, a plurality of direct reception signals are obtained by respectively receiving a plurality of first ultrasonic signals respectively transmitted by each of the first piezoelectric elements, and the average value thereof is used as a reference signal. Consequently, in an ultrasonic diagnostic device configured in this manner, even if there are variations in the properties of the plurality of first piezoelectric elements attributable to, for example, the production process or deterioration over time, these variations among elements are alleviated, allowing the obtaining of a more suitable reference signal.

In addition, in the above-mentioned ultrasonic diagnostic device of another aspect, the first piezoelectric portion is provided with a plurality of first piezoelectric elements, and the reference signal generation unit mutually compares each waveform of a plurality of direct reception signals obtained by respectively receiving a plurality of first ultrasonic signals respectively transmitted by the plurality of first piezoelectric elements prior to being transmitted to the subject, and generates the reference signal by using as the reference signal the direct reception signal for which there is the greatest number of frequencies whose waveforms are mutually identical roughly.

In an ultrasonic diagnostic device configured in this manner, in the case the first piezoelectric portion is formed by being provided with a plurality of first piezoelectric elements, a plurality of direct reception signals are obtained by respectively receiving a plurality of first ultrasonic signals respectively transmitted by each of the first piezoelectric elements, and the direct reception signal among the plurality of direct reception signals having the waveform that occurs most frequently (median value waveform) is used as a reference signal. Consequently, an ultrasonic diagnostic device configured in this manner allows, in a plurality of first piezoelectric elements, the obtaining of more suitable reference signal by alleviating variations among the elements even if there are variations in the properties of the elements attributable to, for example, the production process or deterioration over time.

In addition, in the above-mentioned ultrasonic diagnostic device of another aspect, the second piezoelectric portion is arranged in close proximity to the first piezoelectric portion.

In an ultrasonic diagnostic device configured in this manner, the second piezoelectric portion is arranged in close proximity to the first piezoelectric portion. Consequently, in an ultrasonic diagnostic device configured in this manner, a first ultrasonic signal can be received more directly prior to being transmitted to a subject, and a direct reception signal can be obtained in which external disturbances and noise, for example, are reduced. Thus, a more suitable reception signal is obtained.

In addition, in the above-mentioned ultrasonic diagnostic device of another aspect, the second piezoelectric portion is arranged between the transmission-reception plane of the first and second ultrasonic signals and the first piezoelectric portion.

In an ultrasonic diagnostic device configured in this manner, the second piezoelectric portion is arranged between the transmission/reception plane of the first and second ultrasonic signals and the first piezoelectric portion. Consequently, in an ultrasonic diagnostic device configured in this manner, the second piezoelectric portion is laminated directly or indirectly on the first piezoelectric portion, and the first ultrasonic signal prior to be transmitted to a subject can be received more directly, thereby allowing the obtaining of a direct reception signal in which external disturbances and noise, for example, are reduced. Thus, a more suitable reception signal is obtained.

In addition, in the above-mentioned ultrasonic diagnostic device of another aspect, the second piezoelectric portion is composed by being provided with an organic piezoelectric material.

In an ultrasonic diagnostic device configured in this manner, the second piezoelectric portion is composed by being provided with an organic piezoelectric material. Consequently, an ultrasonic diagnostic device configured in this manner allows ultrasonic signals to be received over a comparative wide band. Thus, an ultrasonic diagnostic device configured in this manner is able to receive a second ultrasonic signal of a higher harmonic wave in response to a prescribed fundamental wave of a first ultrasonic signal, for example, and an ultrasonic image can be formed by, for example, so-called harmonic imaging technology.

This application is based on Japanese Patent Application No. 2009-64145 filed on Mar. 17, 2009, the contents of which are included in the present application.

Although the present invention has been suitably and adequately explained in the above-mentioned description through embodiments thereof with reference to the drawings in order to express the present invention, it should be recognized that the embodiments can be easily altered and/or modified by a person with ordinary skill in the art. Thus, alterations or modification of embodiments carried out by a person with ordinary skill in the art are interpreted to be included within the scope of the claims provided the alterations or modifications are of a degree that does not deviate from the scope of the rights of the claims.

The invention claimed is:
1. An ultrasonic diagnostic device, comprising:
  (i) an image processor;
  (ii) an ultrasonic probe comprising first and second piezoelectric portions that are formed of a piezoelectric material;
  (iii) a reference signal generation circuit;
  (iv) a transmission unit including a circuit which supplies an electric transmission signal to the ultrasonic probe for generating a first ultrasonic signal in the ultrasonic probe;
  wherein the first piezoelectric portion transmits the first ultrasonic signal based on the electrical transmission signal, and wherein the second piezoelectric portion directly receives the transmitted first ultrasonic signal prior to the first ultrasonic signal being transmitted to a subject, generates an electrical direct reception signal based on the directly received first ultrasonic signal, and outputs the generated direct reception signal to a reference signal generation circuit and wherein the second piezoelectric portion receives a second ultrasonic signal generated by reflection of the first ultrasonic signal inside the subject and outputs an electrical reception signal based on the received second ultrasonic signal; and
  wherein the reference signal generation circuit generates a reference signal used in a correlation processing for detecting the second ultrasonic signal based on the direct reception signal generated by the second piezoelectric portion;
  (v) a reception unit including a circuit that receives the electrical reception signal from the ultrasonic probe and outputs a reception signal to the image processor; and
  (vi) a matched filter which carries out the correlation processing between the electrical reception signal based on the second ultrasonic signal and the reference signal generated by the reference signal generation circuit;
  wherein the image processor forms an image based on the second ultrasonic signal detected as a result of correlation processing.

2. The ultrasonic diagnostic device according to claim 1, wherein:
  the first piezoelectric portion comprises a plurality of first piezoelectric elements, and
  the reference signal generation circuit averages a plurality of direct reception signals generated by respectively directly receiving a plurality of the first ultrasonic signals respectively transmitted by the plurality of first piezoelectric elements, and uses the average value as the reference signal.

3. The ultrasonic diagnostic device according to claim 1, wherein:
  the first piezoelectric portion comprises a plurality of first piezoelectric elements, and
  the reference signal generation circuit mutually compares each waveform of a plurality of direct reception signals generated by respectively directly receiving a plurality of first ultrasonic signals respectively transmitted by the plurality of first piezoelectric elements, and generates the reference signal by using as the reference signal a direct reception signal having a waveform that demonstrates a highest frequency.

4. The ultrasonic diagnostic device according to claim 1, wherein the second piezoelectric portion is laminated directly or indirectly on the first piezoelectric portion.

5. The ultrasonic diagnostic device according to claim 4, wherein the ultrasonic probe includes a transmission-reception plane of the first and second ultrasonic signals, and wherein the second piezoelectric portion is arranged between the transmission-reception plane and the first piezoelectric portion.

6. The ultrasonic diagnostic device according to claim 1, wherein the second piezoelectric portion comprises an organic piezoelectric material.

7. The ultrasonic diagnostic device according to claim 1, wherein the second piezoelectric portion includes:
   a first portion which receives the second ultrasonic signal generated by the reflection of the first ultrasonic signal inside the subject and outputs the electrical reception signal based on the received second ultrasonic signal, and
   a second portion which directly receives the transmitted first ultrasonic signal prior to the first ultrasonic signal being transmitted to the subject, generates the electrical direct reception signal based on the directly received first ultrasonic signal, and outputs the generated direct reception signal to the reference signal generation circuit, wherein the first and second portions are separate from each other.

8. The ultrasonic diagnostic device according to claim 1, wherein the second piezoelectric portion includes a portion which both:
   receives the second ultrasonic signal generated by the reflection of the first ultrasonic signal inside the subject and outputs the electrical reception signal based on the received second ultrasonic signal, and
   directly receives the transmitted first ultrasonic signal prior to the first ultrasonic signal being transmitted to the subject, generates the electrical direct reception signal based on the directly received first ultrasonic signal, and outputs the generated direct reception signal to the reference signal generation circuit.

9. The ultrasonic diagnostic device according to claim 1, wherein the second piezoelectric portion is laminated directly over the first piezoelectric portion via an intermediate layer, wherein the intermediate layer matches an acoustic impedance of the first piezoelectric portion and the second piezoelectric portion.

* * * * *